(12) United States Patent
Smith, Jr.

(10) Patent No.: US 7,878,996 B2
(45) Date of Patent: Feb. 1, 2011

(54) LUMBAR SELECTIVE STABILIZATION SUPPORT/BRACE

(75) Inventor: Louis Voigt Smith, Jr., Tomahawk, WI (US)

(73) Assignee: Backsmith, Sterling, IL (US)

( * ) Notice: Subject to any disclaimer, the term of this patent is extended or adjusted under 35 U.S.C. 154(b) by 0 days.

(21) Appl. No.: 12/687,603

(22) Filed: Jan. 14, 2010

(65) Prior Publication Data

US 2010/0121240 A1      May 13, 2010

Related U.S. Application Data

(60) Continuation-in-part of application No. 12/409,131, filed on Mar. 23, 2009, now abandoned, which is a division of application No. 11/247,472, filed on Jan. 3, 2006, now Pat. No. 7,507,214.

(51) Int. Cl.
    *A61F 5/00*     (2006.01)
(52) U.S. Cl. ............................................. 602/19; 602/5
(58) Field of Classification Search ....................... 602/4, 602/5, 19; 128/874–875
    See application file for complete search history.

(56) References Cited

U.S. PATENT DOCUMENTS

| | | | | |
|---|---|---|---|---|
| 5,040,524 A | * | 8/1991 | Votel et al. | 602/19 |
| 5,267,948 A | * | 12/1993 | Elliott | 602/19 |
| 5,722,940 A | * | 3/1998 | Gaylord et al. | 602/19 |
| 6,190,342 B1 | * | 2/2001 | Taylor | 602/19 |

* cited by examiner

*Primary Examiner*—Michael A. Brown
(74) *Attorney, Agent, or Firm*—Banner & Witcoff, Ltd.

(57) ABSTRACT

A lumbar support device and a selective stabilization support device for use in treating mechanical back pain. The lumbar support device includes a torso belt for positioning around the user's mid-section. At least two and typically three straps are also provided connectable at first and second end regions to a surface of the torso belt. Straps are provided to encircle the user's torso to maintain the lumbar support device in position and to engage and maintain in position a pressure appliance arm having a pressure pad thereon. The pressure pad is may thus be configured and precisely positioned to relieve symptoms of back pain.

20 Claims, 12 Drawing Sheets

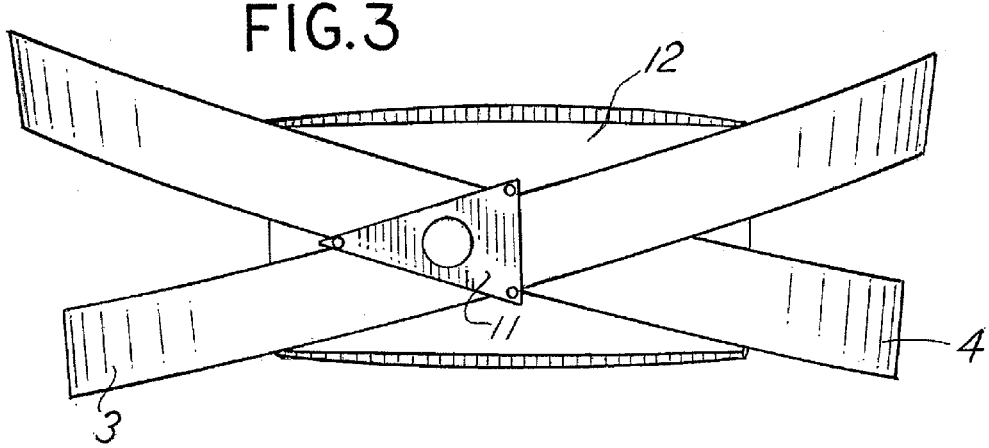
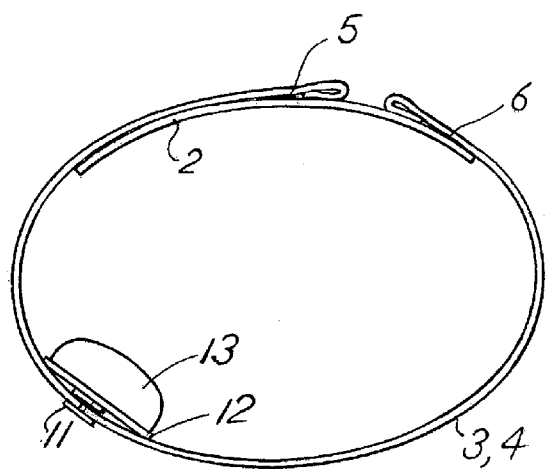 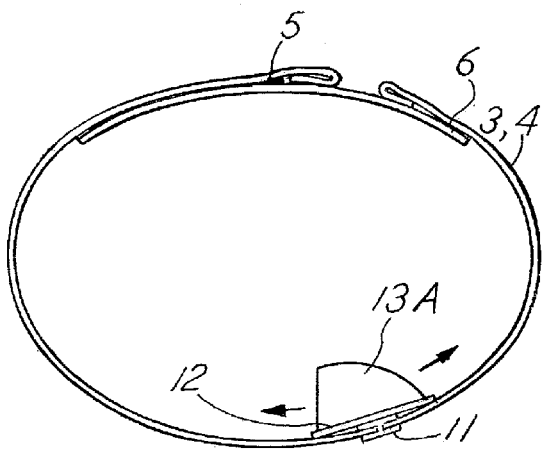
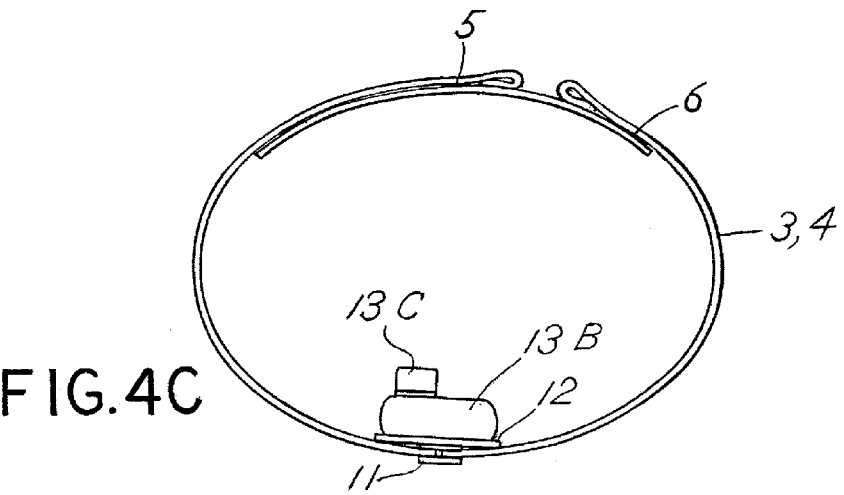

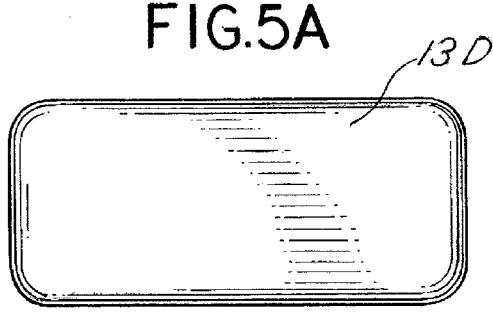
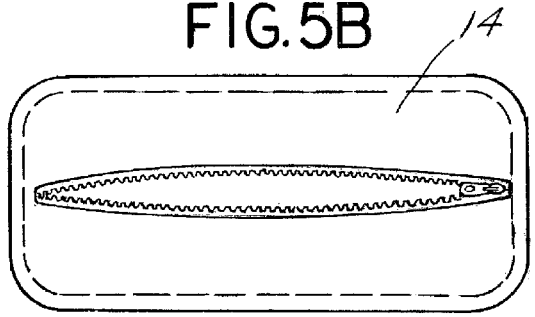
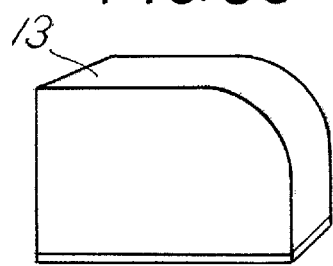
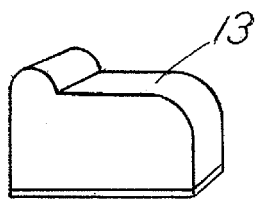
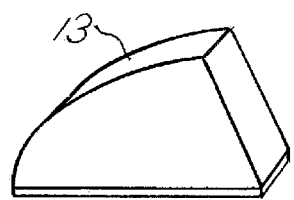
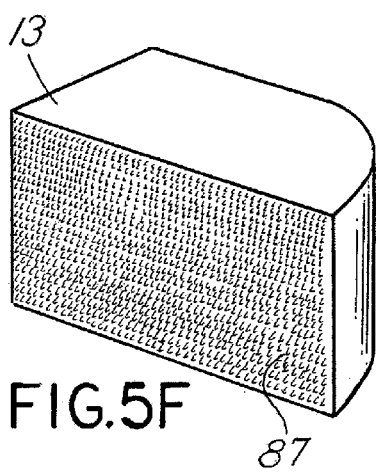
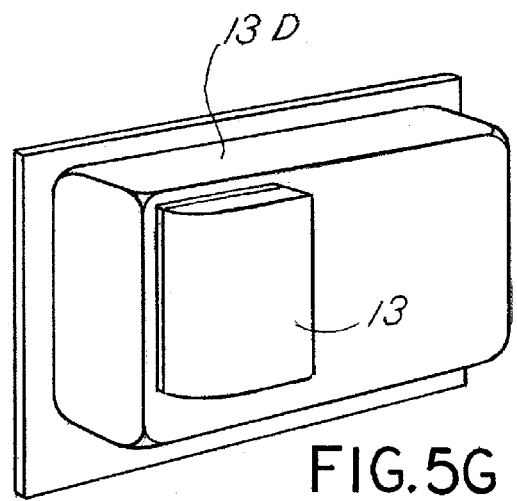

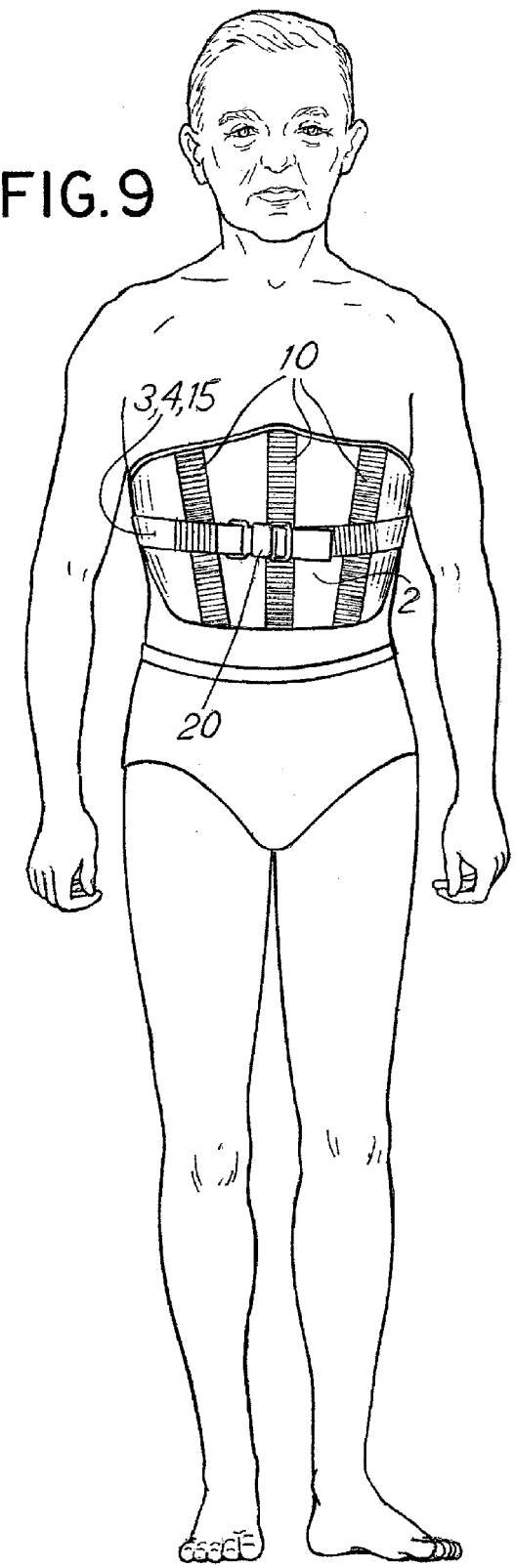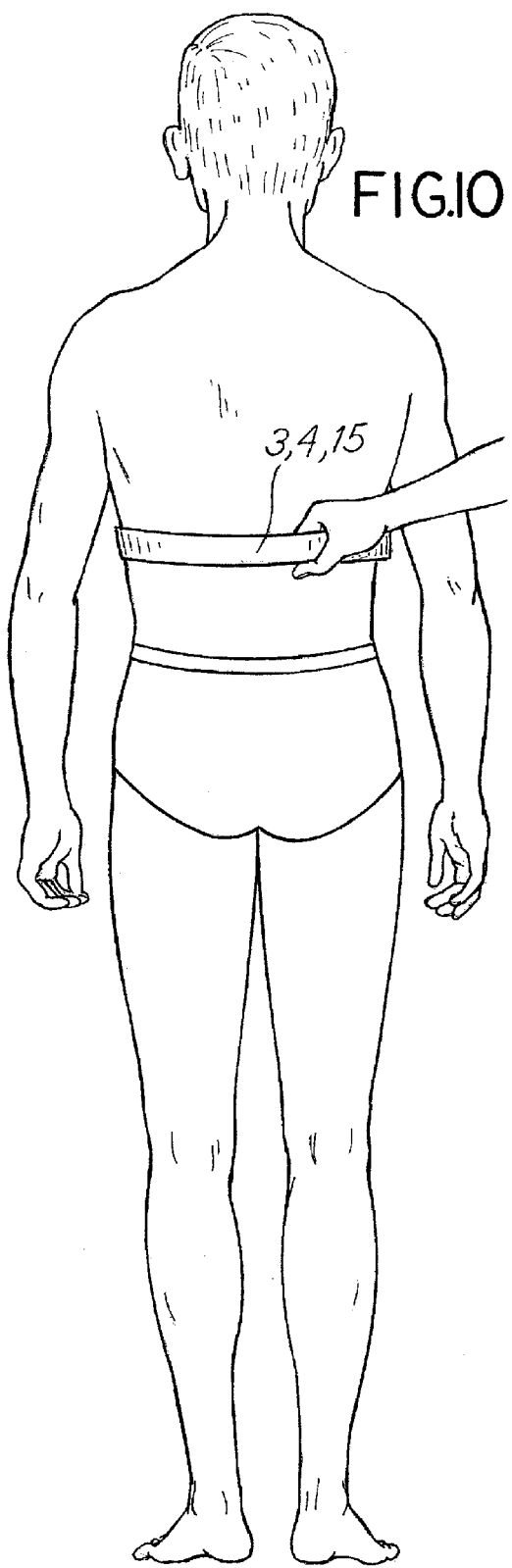

FIG.13
FIG.14
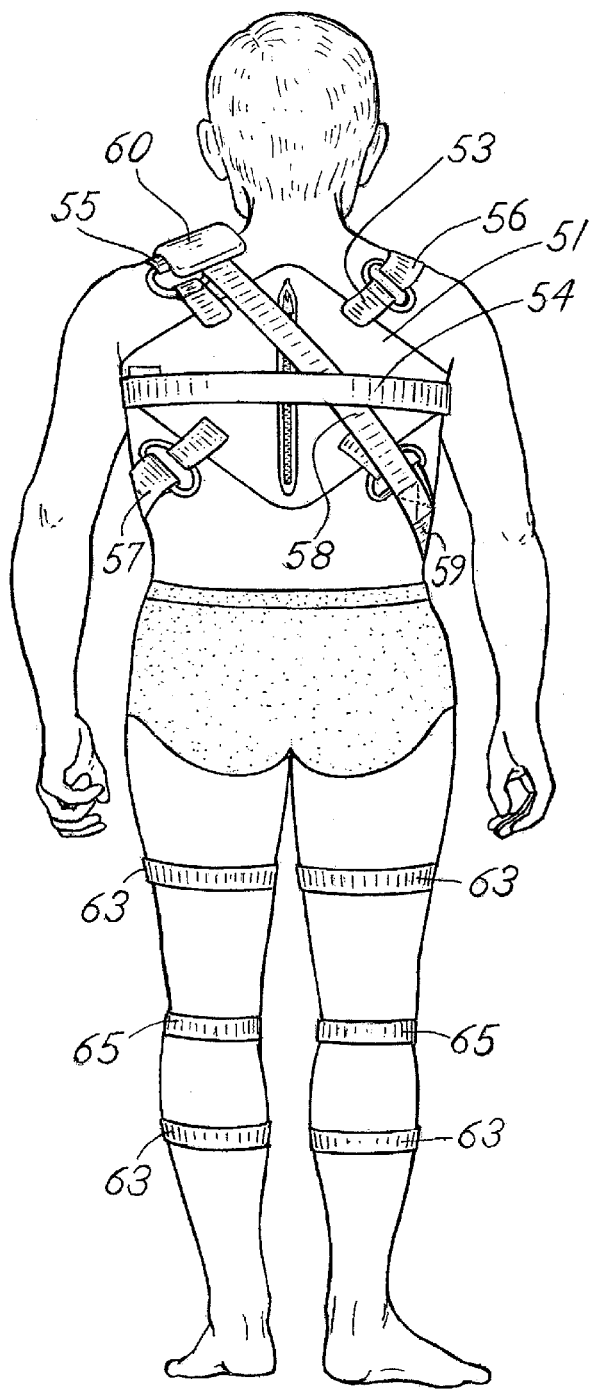
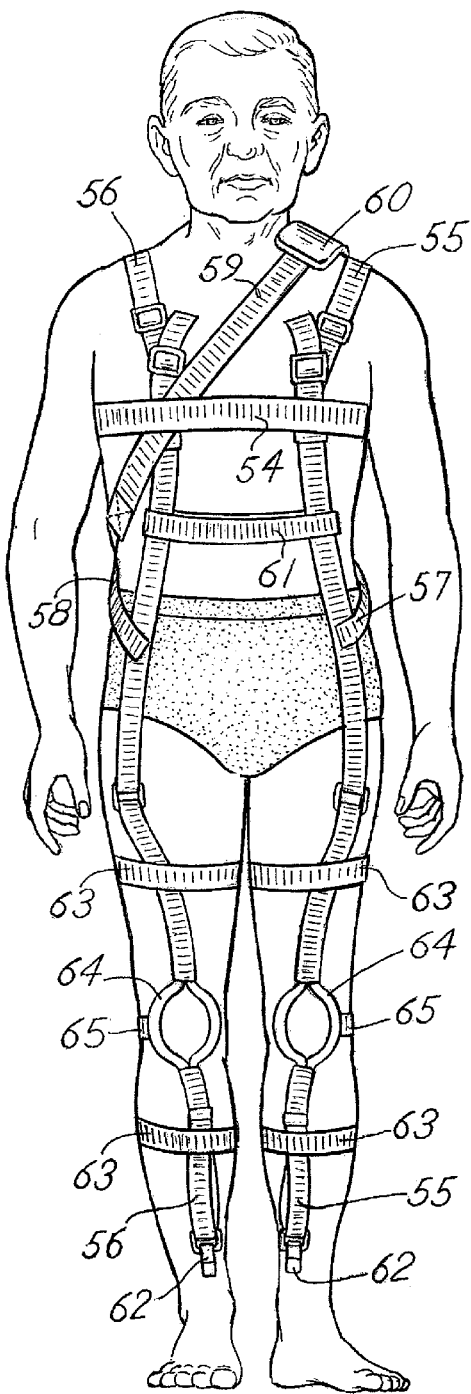

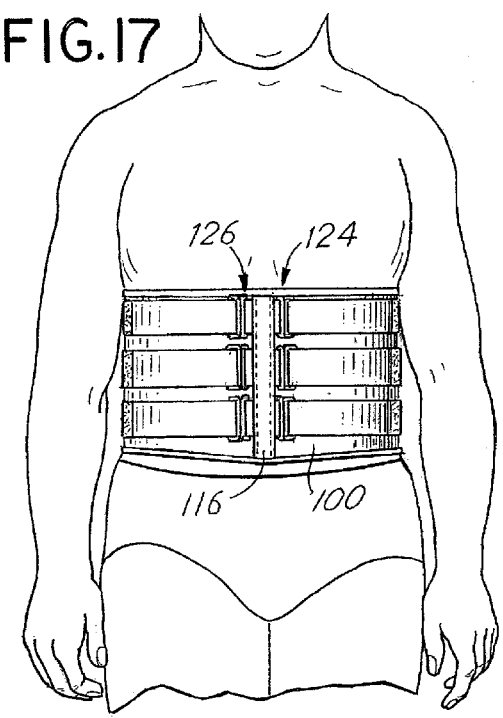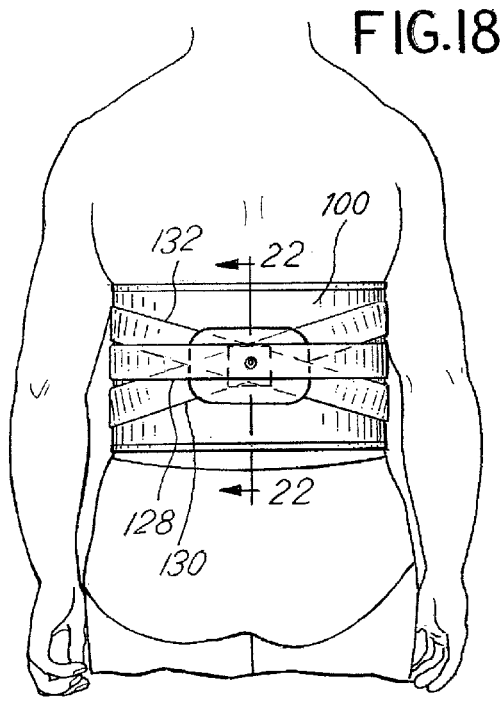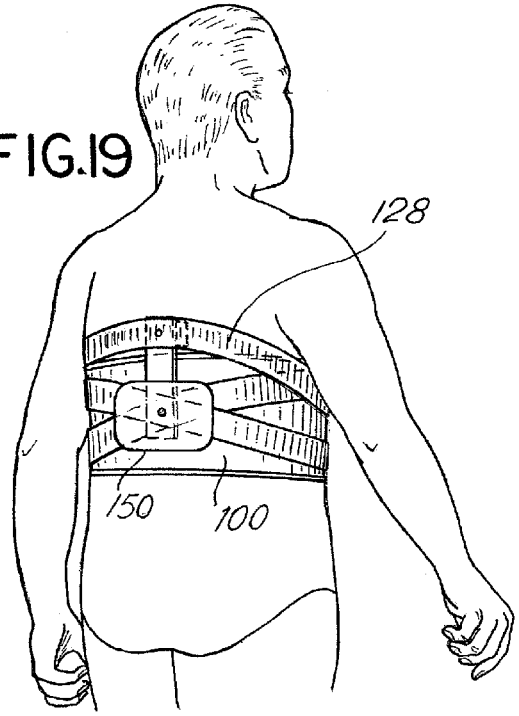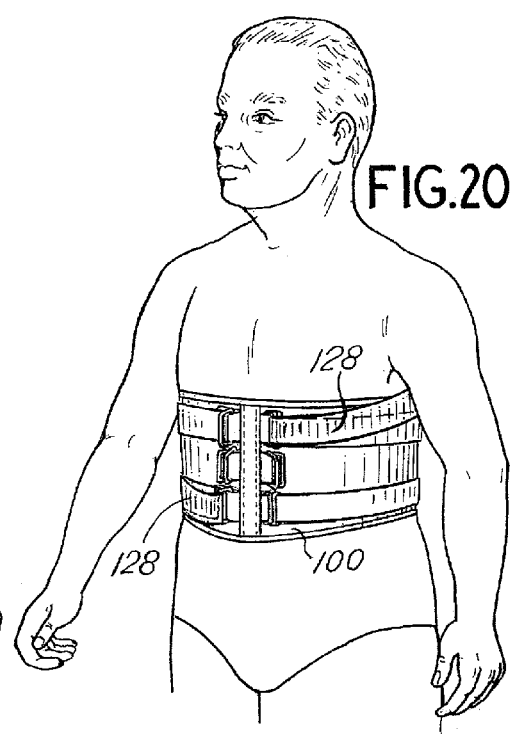

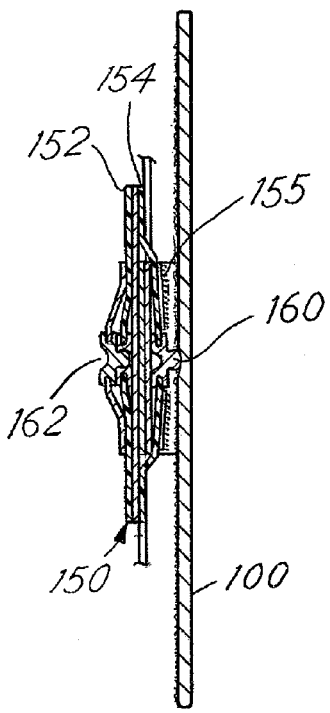
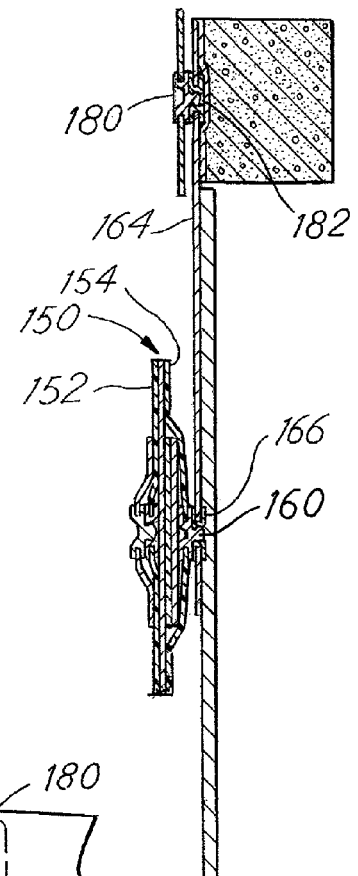
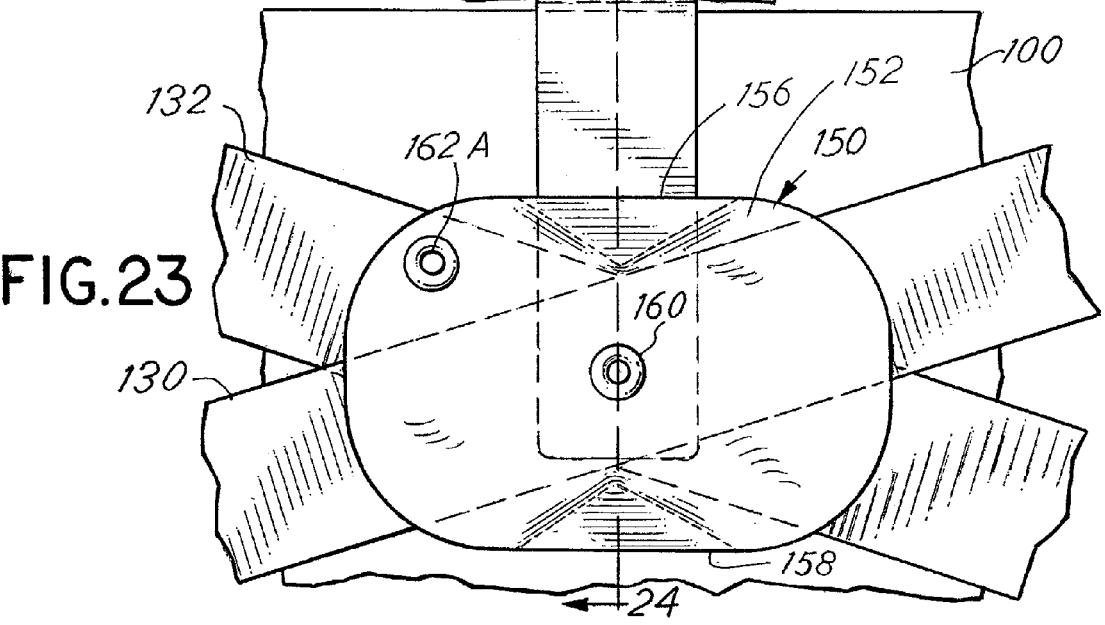

LUMBAR SELECTIVE STABILIZATION SUPPORT/BRACE

CROSS REFERENCE TO A RELATED APPLICATION

This is a continuation-in-part application of Ser. No. 12/409,131 entitled "Lumbar Selective Stabilization Support Brace", filed Mar. 23, 2009, which is a division of Ser. No. 11/247,472 filed Oct. 11, 2005, now U.S. Pat. No. 7,507,214 entitled "Lumbar Selective Stabilization Support/Brace" each of which is incorporated herewith by reference and for which priority is claimed.

BACKGROUND OF THE INVENTION

In a principal aspect the present invention relates to a lumbar support device, a selective stabilization support device and a method of treating mechanical lower back pain using a lumbar support device. In particular, the present invention relates to a versatile lumbar support device and a versatile selective stabilization support device for providing selective stabilization of a localized area of a patient's back or neck.

Mechanical back pain is a problem that affects a large proportion of the population at some point in their lives. The pain often occurs as a result of damage to the discs that are provided between the vertebrae in the spine. Damage to these discs can, in turn, result in more pressure being applied to nerve roots, which leads to pain. As people get older, the discs lose hydration and tend to narrow, thus increasing the pressure on the nerve roots. In younger people, the fibers that form the outer walls of the intervertebral discs can become damaged, resulting in fissures in the outer walls of the discs. As the fibers break down, the gel-like substance contained within the disks leaks out, reducing the effectiveness of the discs and increasing the pressure on the surrounding nerves and ligaments. The resulting instability can reduce or block a patient's range of movement and cause pain, weakness and sensory changes. Another cause of back pain is spondylolisthesis, an instability caused by the shifting of one vertebra over another. These types of damage to the spine often occur gradually as a result of poor posture and excessive bending of the back.

At present, mechanical back pain such as that described above is often treated by prescribing drugs to the patient. However, although drugs may reduce the pain experienced by the patient and may reduce the inflammation, they do not address the underlying cause of the pain. Furthermore, surgery is sometimes used to address problems in the spine, for example to remove a damaged segment and to fuse the neighboring vertebrae. Surgery, however, is expensive and invasive, and often does not provide a long lasting solution.

In addition, methods and devices are known for rigidly bracing a patient's back, such as that disclosed in U.S. Pat. No. 5,259,831 for applying rigid thermoplastic panels to the chest and back of a patient to brace the patient's back. The panels provide general support over a large region of the patient's back, but severely restrict the movement of the patient.

Furthermore, devices are also known for providing general support to the lower back region to reduce the likelihood of damage occurring or to treat injury. For example, U.S. Pat. No. 6,319,217 discloses a lumbosacral support pad comprising a moisture-curable resin that hardens upon curing to form a rigid structure that retains its post-curing shape. The support pad is cured in situ on the patient's back such that the resin adopts the contours of the patient's back. Thereafter, the support pad provides general support over the lumbar region of the patient's back. In U.S. Pat. No. 6,666,838 there is disclosed a low profile lumbo-sacral orthosis for providing general support to a patient's back to reinforce proper body ergonomics.

These prior art devices are, however, only able to provide general support over the patient's lumbar region. In treating disc derangement, it is desirable to centralize the pain and to therefore reduce the extent of peripheralization, which is the radiation of the pain from a central region to distal regions of the body. For example, back pain may radiate down a patient's legs or other regions.

A known and respected technique for helping to analyze and treat a patient's back pain is the McKenzie Approach. The McKenzie approach involves an organized and systematic mechanical evaluation, categorization and treatment technique for helping to centralize and manage a patient's back pain. According to this approach, the patient's back pain is analyzed by considering the patient's history of back pain, their symptoms, the factors that aggravate or improve the pain and by classifying the pain according to a series of sub-classifications. The McKenzie approach can be used, for example, to determine whether a patient has a central lesion of a disc, or a lesion to one side of the disc, and can help categorize mechanical lesions. Furthermore, the McKenzie approach is used to determine the optimum locations, directions and quantities of pressure to apply to selected locations on the patient's back in order to stabilize and centralize the pain.

The patient can then be maneuvered into particular positions by a therapist to help to centralize the pain. This approach is generally successful at helping to reduce a patient's symptoms. However, it is not possible to maintain a patient in these positions such that they are provided with selective stabilization of localized regions of the back for a prolonged period of time. Furthermore, the prior art devices outlined above are not able to provide versatile selective stabilization.

It is therefore desirable to provide support devices that are capable of providing the necessary localized support to selected regions of a patient's back. Furthermore, it is desirable that such support devices be easy to don and doff, comfortable to wear and configurable to different configurations so as to provide the desired support.

SUMMARY OF THE INVENTION

Briefly, the present invention comprises a lumbar support device for providing localized support to a lumbar region of a user comprises: a semi-rigid member for positioning around the user's abdomen, the member being shaped to generally conform with the contours of the user's abdomen; at least one tensioning strap connectable at first and second end regions to attachment means provided on a surface of the semi-rigid member, the at least one tensioning strap being provided to encircle the user's torso so as to maintain the lumbar support device in position; a clip slidably mounted on the at least one tensioning strap, the clip being movable along the at least one tensioning strap; a pad base mounted on the clip, the pad base being movable with the clip along the at least one tensioning strap such that its position at the lumbar region of the user can be varied; and at least one pad mounted on the pad base, the at least one pad being provided to apply pressure to a localized area of the user's lumbar region.

In one embodiment, two tensioning straps are provided, the tensioning straps crossing at the clip. In addition, the clip is preferably a triangular adjustment clip through which the two tensioning straps pass.

In another embodiment, an additional tensioning strap is provided, the additional tensioning strap being connectable at first and second end regions to the surface of the semi-rigid member and being provided with an adjustable attachment means, such as another clip. Another pad base may be mounted on the adjustable attachment means.

In a still further embodiment, the attachment means comprises one or more adhesive strips provided on a front surface of the semi-rigid member, the adhesive strips engaging with material provided at the said first and second end regions of the said at least one tensioning strap.

In addition, the at least one pad is preferably attached to the pad base by means of an adhesive material, such that it is detachable from the pad base. The at least one pad may comprise a compressible material, such as a foam or rubber material. Preferably, the at least one pad is selected from a group of pads having a range of different shapes, sizes and densities. Selection of the at least one pad is made depending upon the location to which it is to be applied and the required pressure to be applied.

Furthermore, the semi-rigid member may comprise a molded base plate having a generally curved shape so as fit comfortably around the user's abdomen.

In a further embodiment, the lumbar support device may further comprise a pair of stabilizing straps, each stabilizing strap being attached at a first end to the pad base or at least one pad and at a second end to the surface of the semi-rigid member. In use, each stabilizing strap passes under the user's crotch. These straps help to maintain the lumbar support device in the desired orientation on the user's body. In particular, they prevent the device from sitting too far (high) up the user's torso.

In a still further embodiment, one or more additional pads may be attached to the at least one tensioning strap at different positions along the strap. Suitable means may be provided on the tensioning strap or straps for attachment of the additional pad or pads. The means may, for example, comprise regions of adhesive material provided on the tensioning strap or straps.

The tensioning strap or straps enable the lumbar support device to be securely fitted around the user's body, such that the device does not slip from its optimal position. Furthermore, adjustment of the straps helps to enable a desired force to be exerted from the pad or pads on the selected localized regions of the patient's back.

According to a second aspect of the invention, there is provided a lumbar support device for providing localized support to a lumbar region of a user, comprising: a semi-rigid member for positioning around the user's abdomen, the member being shaped to generally conform with the contours of the user's abdomen; at least two tensioning straps, the tensioning straps being provided to encircle the user's torso so as to maintain the lumbar support device in position, each said tensioning strap being connectable at first and second end regions to the semi-rigid member, the said tensioning straps being connected by a single, adjustable attachment element to at least one compressible pad, the at least one compressible pad being provided to apply pressure to a localized area of the user's lumbar region.

According to an embodiment of the lumbar support device according to the second aspect of the invention, the said tensioning straps cross over at the said single, adjustable attachment element.

Furthermore, according to a further embodiment of the lumbar support device, the said single, adjustable attachment element comprises a triangular adjustment clip, through which the said tensioning straps pass, and a pad base attached to the triangular adjustment clip and to the at least one pad.

In an alternative embodiment of the lumbar support device, the said single, adjustable attachment element comprises a pad supporting material in which a pad support is wrapped, the pad supporting material being tied around the said tensioning straps such that the pad support can be moved along the tensioning straps to the desired lumbar region of the user.

In a still further embodiment of the lumbar support device, the attachment means comprises one or more adhesive strips provided on a front surface of the semi-rigid member, the adhesive strips engaging with material provided at the first and second end regions of the tensioning straps.

In addition, the at least one compressible pad preferably comprises a foam or rubber material.

According to a third aspect of the invention, there is provided a lumbar support device for providing localized support to a lumbar region of a user, comprising: a semi-rigid member for positioning around the user's abdomen, the member being shaped to generally conform with the contours of the user's abdomen; at least two tensioning straps, the tensioning straps being provided to encircle the user's torso so as to maintain the lumbar support device in position, each said tensioning strap being connectable at first and second end regions to the semi-rigid member and each tensioning strap being connected by an adjustable attachment element to a pad support; and at least one pad connected with the pad support, the at least one pad being provided to apply pressure to a localized area of the user's lumbar region.

According to an embodiment of the above lumbar support device, the at least two tensioning straps are connected to the same pad support.

According to an alternative embodiment of the above lumbar support device, each of the tensioning straps is connected to a separate pad support.

According to a fourth aspect of the invention, there is provided a selective stabilization support device for providing localized support to a mid-back region of a user, comprising: a base pad for providing localized support to the mid-back region of the user; a holder in which the base pad is contained, the holder being provided with attachment means; two transverse stabilization straps, each connectable at a first end region to the attachment means of the holder and each extending, in use, over a shoulder of the user and substantially vertically down the chest and torso of the user to terminate at a second end region at a leg portion of the user; and two diagonal support straps, each attached at a first end region to the attachment means of the holder and each extending, in use, away from the holder around a side of the user to attach at a second end region to a respective one of the transverse stabilization straps.

According to an embodiment of the selective stabilization support device, a lower neck selective stabilization pad may be attached to one of the transverse stabilization straps or may be provided on a lower neck stabilization strap attached to the holder.

According to another embodiment of the device, a lateral stabilization strap is provided, the lateral stabilization strap being connectable to the attachment means of the holder and extending substantially horizontally around the back and chest of the user in use.

According to another embodiment, the selective stabilization support device further comprises an anterior stabilization strap attached at a first end to one of the transverse stabilization straps and at a second end to the other of the transverse stabilization straps. The anterior stabilization strap may be attached to the transverse stabilization straps by means of an adhesive material.

In a still further embodiment, the second end region of each of the transverse stabilization straps has a clip for attachment to a sock of the user. In addition, one or more leg loop straps may be provided, each being attachable to one of the transverse stabilization straps and, in use, extending around a leg of the user. Furthermore, each transverse stabilization strap may form a loop section around the user's knee, so as not to restrict the user's range of movement.

Preferably, the attachment means provided on the holder comprises regions of adhesive material for attachment to suitable material provided on the straps. In this way, the various straps can be attached and released as desired, enabling different sizes (lengths) of straps to be attached to a particular pad and holder. Alternatively, some or all of the straps may be attached to the pad holder using clips, particularly metal or plastic clips.

Furthermore, the straps are preferably adjustable using adjustment means provided on the straps, such that the lengths of the straps may be adjusted to suit the particular user, and to ensure that the straps are taut in use. Suitable adjustment means may be buckles such as those found on life vests.

According to a fifth aspect of the invention, there is provided a method of applying a lumbar support device to treat mechanical lower back pain of a patient, the method comprising: determining that the back pain is mechanical in origin; evaluating the nature and location of the pain; classifying the pain according to a classification system; positioning a semi-rigid member of the lumbar support device around the user's abdomen, the member being shaped to generally conform with the contours of the user's abdomen; adjusting at least one tensioning strap connected at first and second end regions to a surface of the semi-rigid member, the at least one tensioning strap encircling the user's torso so as to maintain the lumbar support device in position; selecting a pad having a particular size, shape and density for attachment to the at least one tensioning strap; adjusting the position of the pad relative to the lumbar region of the patient, such that the pad is positioned at a selected localized area of the lumbar region of the patient; and adjusting the tension of the at least one tensioning strap to exert a desired amount of pressure on the localized area using the pad.

According to the fifth embodiment of the invention, a lumbar support device is used in conjunction with the McKenzie approach for determining the nature of mechanical lower back pain to treat the pain. By combining the lumbar support device with such an approach (or other techniques), effective treatment can be provided. Furthermore, a similar method of treatment may be provided by combining the selective stabilization support device with the McKenzie Approach, with physical therapy spinal stabilization exercises or other suitable approaches.

BRIEF DESCRIPTION OF THE DRAWING

In the detailed description which follows, reference will be made to the drawing comprised of the following figures:

FIG. 3 shows the tensioning straps, clip and pad base of the lumbar support device of the first embodiment;

FIGS. 4A to 4C show views of the lumbar support device from above, with the clip and pad base provided at different positions and with different pads attached;

FIGS. 5A to 5G show various pad base and pad configurations;

FIG. 9 is a frontal view of a user wearing a lumbar support device according to a third embodiment;

FIG. 10 is a rear view of the user wearing the lumbar support device according to the third embodiment;

FIG. 13 is a rear view of a user wearing a stabilization support device according to a fifth embodiment of the invention;

FIG. 14 is a front view of the user wearing the stabilization support device according to the fifth embodiment of the invention;

FIG. 17 is a frontal view illustrating the positioning of a further example or embodiment of the invention comprising a torso belt in combination with a strap assembly and a pressure appliance arm on an individual;

FIG. 18 is a backside elevation of the lumbar support of the type depicted in FIG. 17 wherein the pressure appliance arm is removed from the embodiment;

FIG. 19 is a partial side perspective view of the embodiment of FIG. 17 illustrating the inclusion of the pressure appliance arm in the combination;

FIG. 20 is partial side perspective view of the lumbar support construction of FIG. 19;

FIG. 22 is a cross sectional view of the torso belt in combination with a pressure pad taken along the line 22-22 in FIG. 18;

FIG. 23 is a partial backside elevation of the lumbar support embodiment of FIG. 19 inclusive of the pressure appliance arm;

FIG. 24 is a sectional view taken along the line 24-24 of FIG. 23; and

DESCRIPTION OF THE PREFERRED EMBODIMENT

Figure 1:
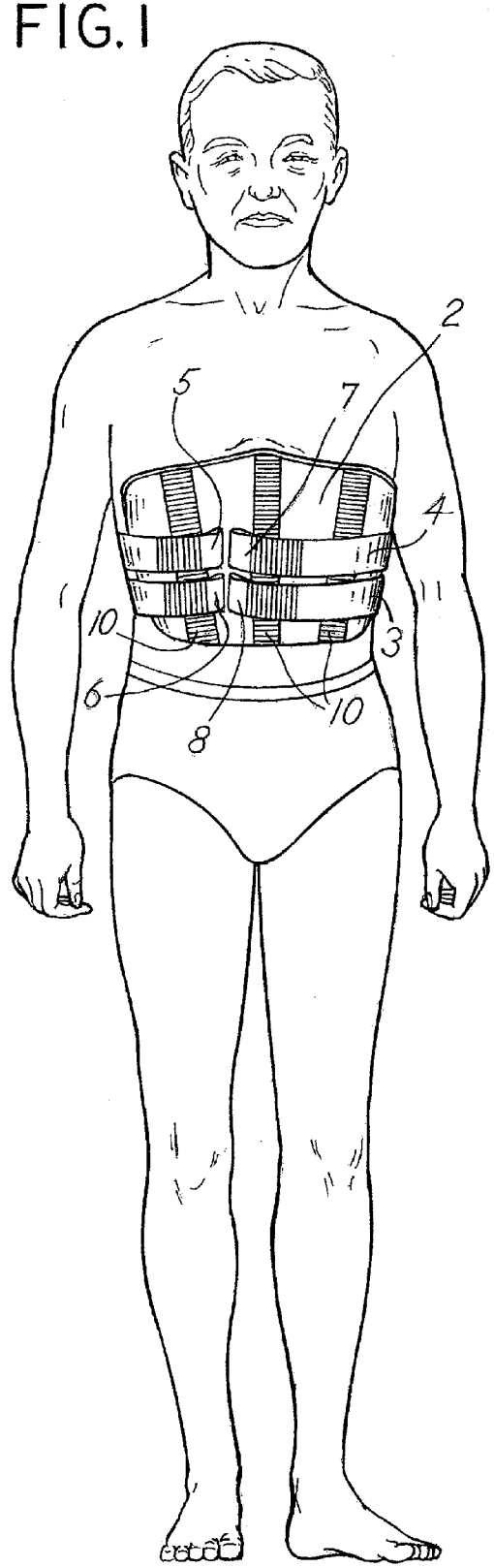
FIG. 1 is a frontal view of a user wearing a lumbar support device according to a first embodiment.
Figure 2:
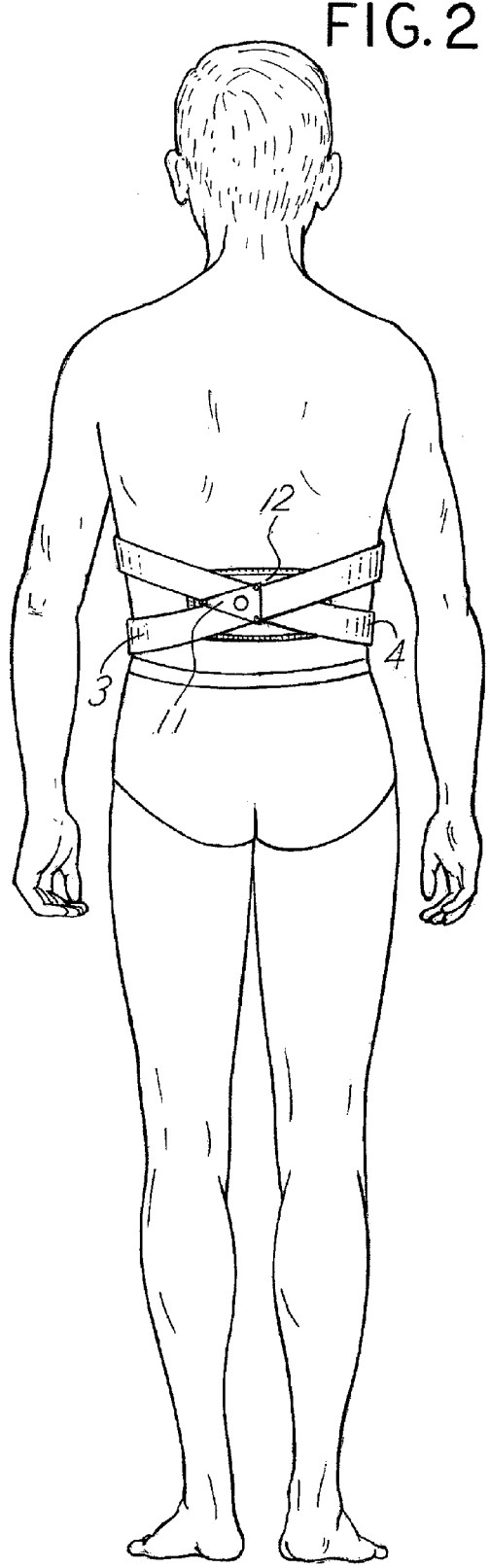
FIG. 2 is a rear view of the user wearing the lumbar support device of the first embodiment.

Referring to the figures, FIGS. 1 and 2 of the accompanying drawings show a lumbar support device according to a first embodiment of the invention. The lumbar support device is used to treat mechanical lower back pain, such as that resulting from disk derangement and spondylolisthesis or other mechanical disorders. In particular, the device provides selective support to a localized area of a patient's lumbar region. Preferably, the device is fitted by a therapist trained in the diagnosis of mechanical lower back pain using the McKenzie approach or any other such technique or approach for diagnosis.

FIG. 1 shows a front view of the device 1 as worn by a user or patient. As can be seen, the device includes a semi-rigid member 2 having a curved shape extending across the abdominal region of the user. Thus, the semi-rigid member is curved so as to generally conform to the contours of the user's abdomen. The semi-rigid member 2 may comprise a molded base plate, such as a molded plastic or thermoplastic plate or panel. Two tensioning straps 3, 4 are provided across the base plate, each tensioning strap being connected at first 5, 6 and second 7, 8 end regions to attachment means 10 located on the front surface of the base plate. The attachment means 10 may comprise regions of adhesive material provided on the front surface of the base plate. More particularly, the attachment means may comprise strips of adhesive material, such as hook and loop fasteners, e.g., Velcro brand fasteners, as shown in the figure.

FIG. 2 shows a rear view of the device 1 worn by the user. It can be seen from this figure that the straps 3, 4 cross over, such that the upper strap 4 on the user's left side becomes the lower strap 4 on the user's right side and the lower strap 3 on the user's left side becomes the upper strap 3 on the user's right side. An adjustable attachment element (means) in the form of a metal adjustor clip 11 is provided at the intersection of the two tensioning straps 3, 4. A pad base 12 is mounted on (attached to) the adjustor clip 11.

The metal adjustor clip 11 is formed of two substantially triangular elements connected to one another at the corner regions, with a gap provided between the elements. A plan view of the clip can be seen in FIG. 3. More particularly, the metal adjustor clip is in the form of an isosceles triangle, with each of the tensioning straps passing through the shorter vertical side and one of the other, longer sides of the triangle, such that the straps cross. The pad base 12 is mounted on the clip acting as the adjustable attachment element. Preferably, the pad base 12 is detachable from the clip. For example, the pad base 12 may be attached by means of an adhesive material to the clip 11. Also the clip 11 may be coated or covered with a molded or formed cover (not shown). The cover would then be stabilized from movement (as would clip 11) by hook and loop fasteners attaching the cover to the straps. This would also facilitate the compression in the lumbar region.

One or more pads 13 can be attached to the pad base, as shown in FIGS. 4A to 4C. The particular number of pads, and the size, shape and density of the pads, can be determined by the therapist fitting the device to the user. In this regard, the therapist may use the McKenzie approach or other such technique for determining the nature of the mechanical lower back pain. Using such a technique, the therapist can determine the localized regions of the user's back to be selectively stabilized using the lumbar support device.

FIG. 4A shows a case where the area to be localized is to the left of the user's spinal column. By sliding the adjustable attachment means (in the form of the clip 11) along the tensioning straps 3, 4, it is possible to vary the position of the pad base 12 in the lumbar region of the user. One or more pads 13 can then be attached to the pad base 12. In the example of FIG. 4A, a single pad 13 is used to provide lateral support to a localized region of the user's back. In FIG. 4B, the clip 11 has been moved to the right of the patient's spine, and a pad 13A has been attached to the pad base 12. It can be seen that the pad 13A is different in size and shape to the pad 13. This is because the particular shape, size and density of each of the pads must be carefully chosen by the therapist to best suit the user's (patient's) particular needs; i.e. to position the pad in a therapeutically desirable position. A further example is shown in FIG. 4C, in which two pads 13B and 13C are mounted on the pad base 12. The additional pad 13C provides added support to the desired localized region of the user's back as appropriate, thus enabling satisfactory selective stability to be achieved.

The pads 13 may comprise a compressible material, such as a foam or rubber material. For example, they may comprise EVA compressed foam and/or urethane foam. The different pad sizes, shapes and densities make it possible to customize significant lateral and/or medial support, such as to provide the lateral or medial support required to help centralize ipsilateral back and leg pain. In particular, the different pads allow for selective stabilization at different levels, and make it possible to provide a large quantity of lateral force (providing posterior to anterior medial support) and/or lateral to medial support.

It can also be seen in FIGS. 4A to 4C that the ends of the straps are looped, thus making them easy to grasp and pull for a user.

FIGS. 5A to 5G show different pad configurations. FIG. 5A shows one possible configuration for a base pad, which is the pad mounted on the pad base. The base pad 13D may be provided with regions of adhesive material to adhere it to the pad base 12 and to enable the attachment of additional pads 13 to it. Alternatively, the base pad 13D may be provided inside of a base pad cover 14, the base pad cover being provided with adhesive regions for connection with the pad base 12 and additional pads 13. Such an arrangement is shown in FIG. 5B, where the base pad is zipped inside the base pad cover 14. FIGS. 5C to 5E show possible alternative shapes for the pads (or base pads) 13. Of course, other shapes are possible, and it is not intended to limit the pads to the particular shapes depicted. FIG. 5F shows an additional pad 13 provided with adhesive material on one surface 87 for attachment to a base pad 13D. As can be seen in FIG. 5G, the additional pad may be attached to the base pad by means of the adhesive material. In a similar manner, the base pad may be attached to the pad base 12 using a region of adhesive material provided on the base pad.

The tension in the tensioning straps 3, 4 can be varied by fastening the said first 5, 6 and second 7, 8 end regions to different ones of the vertical strips of adhesive material (constituting the attachment means) provided on the front surface of the semi-rigid member 2. In addition, the angle of pull of the straps can be altered, depending upon the vertical position of attachment to the strips of adhesive material. This in turn helps to ensure that the device is securely and comfortably fitted, and that the required tension is exerted by the pad or pads 13.

Figure 6:
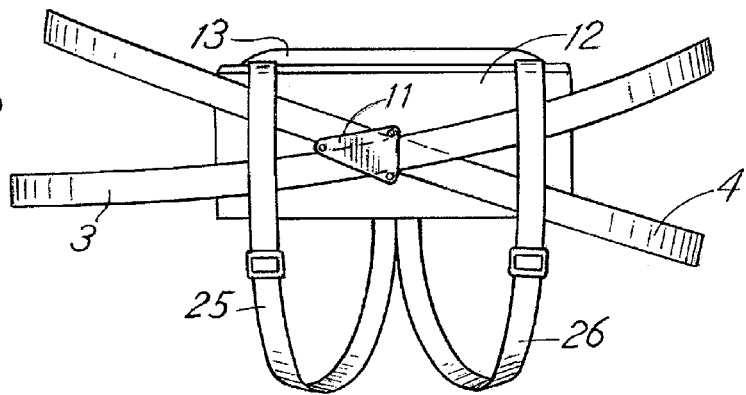
FIG. 6 shows a modification to the lumbar support device of the first embodiment to include a pair of stabilizing straps.

As a modification of the lumbar support device according to the above embodiment, a pair of stabilizing straps 25, 26 may be provided additionally. FIG. 6 shows a rear view of the lumbar support device further comprising a pair of such stabilizing straps. Each strap is attached at a first end to a surface of the semi-rigid member 2 and at a second end to either the pad base 12 or a pad 13. In use, each strap loops under the user's groin from the semi-rigid member provided around the user's abdomen to the pad base or pad provided on the user's lower back. These stabilizing straps help to maintain the lumbar support device in position, and to prevent it from twisting, slipping or riding too high up the user's torso. Thus, they help to maintain the pad or pads in the required position, and also help to maintain the overall orientation of the device, ensuring that it is comfortable for the user.

Figure 7:
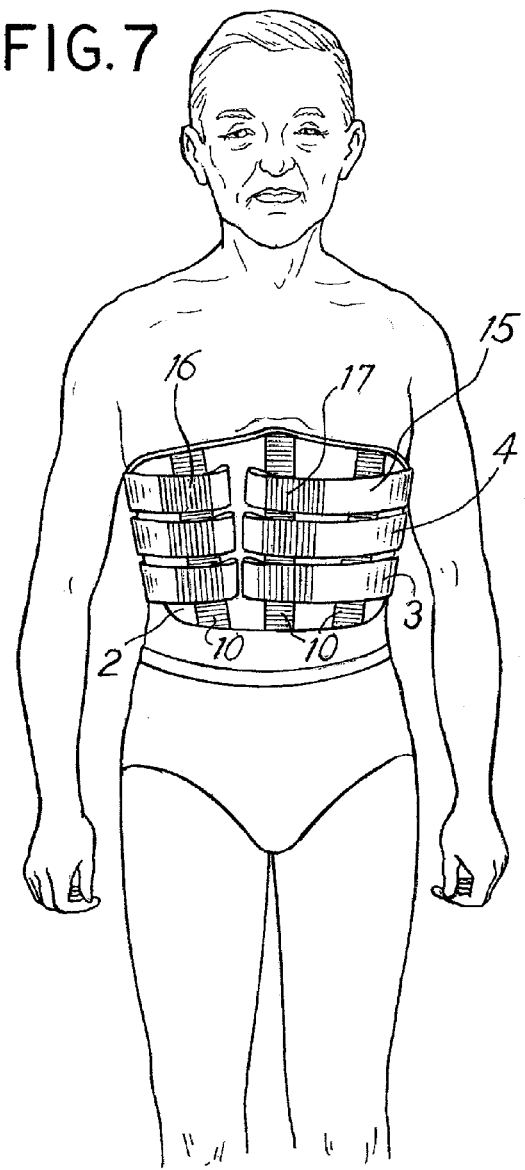
FIG. 7 is a frontal view of a user wearing a lumbar support device according to a second embodiment.
Figure 8:
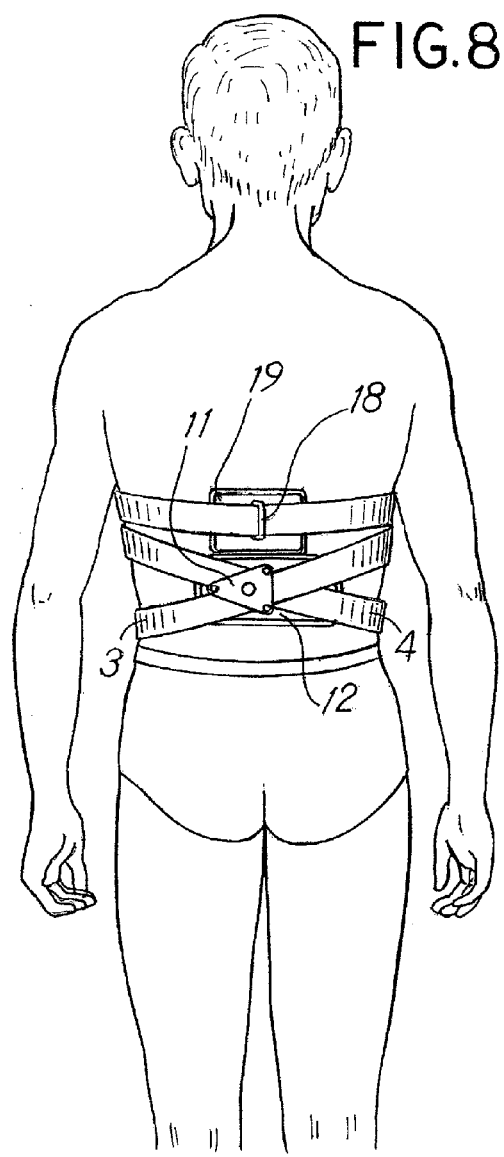
FIG. 8 is a rear view of the user wearing the lumbar support device according to the second embodiment.

FIGS. 7 and 8 show a second embodiment of a lumbar support device according to the invention. According to this embodiment, an additional tensioning strap 15 is provided in addition to the two crossed tensioning straps 3, 4 described above. In other respects, the device is the same as that of the first embodiment. As can be seen from FIG. 7, the additional tensioning strap 15 is connected at first and second end regions 16, 17 to the attachment means 10 provided on the front surface of the semi-rigid member 2. Preferably, the additional tensioning strap can be detached from the semi-rigid member at one or both of its first and second end regions 16, 17. Such a detachable connection may be realized by, for example, providing the attachment means 10 as regions of adhesive material. In particular, as shown in the figure, the attachment means may comprise vertically aligned strips of adhesive material.

FIG. 8 shows a rear view of a user wearing the lumbar support device according to this embodiment. The additional tensioning strap 15 is arranged around the user's body above the two crossed tensioning straps 3, 4. A single, adjustable attachment means 18 is provided on the additional tensioning strap. In the figure, a D-ring is depicted as the adjustable attachment means, although any suitable fastening device may be used. Furthermore; an additional pad base 19 may be mounted on the adjustable attachment means 18 and the additional pad base 19 may be connected at a lower side to an upper side of the pad base 12. Alternatively, a single continuous pad base may be provided, comprising the pad bases 12 and 19 and being attached to both the clip 11 of the two crossed tensioning straps and the adjustable attachment means 18 of the additional tensioning strap.

By providing an additional tensioning strap 15 in this manner, it is possible to hold a larger pad base (with a pad or pads mounted thereon) in position at a desired localized region of a user's back. The additional tensioning strap enables the larger pad base to be held tightly against the user's back, to ensure that the desired support is provided to the selected region. Alternatively, the additional tensioning strap 15 enables a second pad base 19 to be provided on the user's back in addition to the first pad base 12. Furthermore, although in the figure the second pad base is shown at a central region of the user's back, immediately above the first pad base, the position of the second pad base 19 may be varied by moving the single, adjustable attachment means 18 laterally along the additional tensioning strap. In this way, localized support can be provided by the lumbar support apparatus to two quite separate regions of the user's back, providing versatile lateral and medial support functions.

FIGS. 9 and 10 show a third embodiment of the lumbar support device. Here, a single tensioning strap 3, 4, 15 is shown for simplicity. The strap is provided with adjustment means in the form of a buckle 20 to enable the length of the strap around the user's torso to be varied over a larger range than is otherwise possible. The buckle may, for example, be of the type provided on life vests. By providing adjustment means such as buckles 20 on the straps 3, 4 and 15 of the above described first and second embodiments, it is possible to adjust the tension of the straps more precisely, so as to ensure that the desired tension is achieved and maintained and thus that the required force is applied to the selected localized area or areas of the user's back. Furthermore, by providing crossed tensioning straps 3, 4, selective placement of, and the exertion of strong pressure from, the pads 13 can be reliably and effectively realized.

Figure 11:
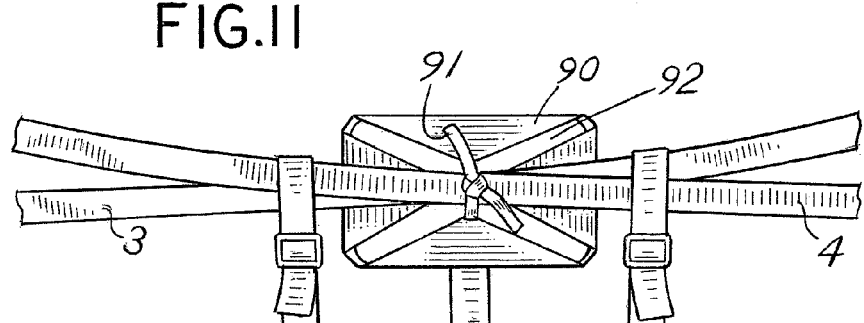
FIG. 11 is a rear view of a lumbar support device according to a fourth embodiment of the invention.

FIG. 11 shows a rear view of a lumbar support device according to a fourth embodiment of the invention. According to this embodiment, a semi-rigid member and two crossed tensioning straps are provided in a similar manner to the first embodiment described above. In addition, a pair of stabilizing straps is provided in a similar manner to that described with reference to FIG. 6 above. Each of the stabilizing straps is attached at a first end to the semi-rigid member and at a second end to one or both of the two crossed tensioning straps (instead of being attached to a pad base or pad). Furthermore, according to the embodiment of FIG. 11, a pad support 92 is connected to the crossed tensioning straps using an adjustable attachment element, the adjustable attachment element being movable along the crossed tensioning straps, so as to enable the position of the pad support with respect to the user's lumbar region to be varied.

Figure 12A:
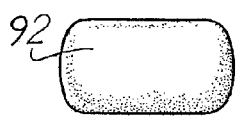
FIGS. 12A to 12D show the constitution of an adjustable attachment element of the lumbar support device of the fourth embodiment.
Figure 12B:
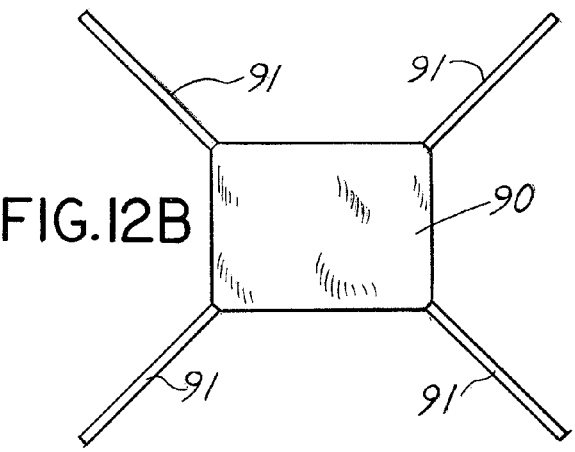
Figure 12C:
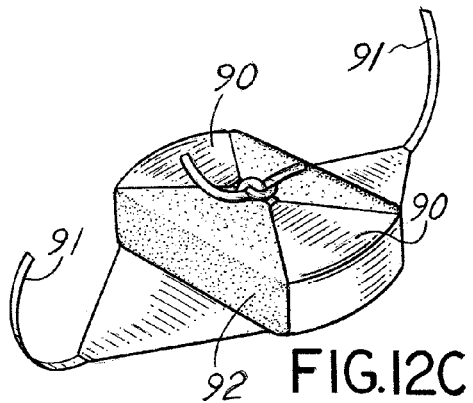
Figure 12D:
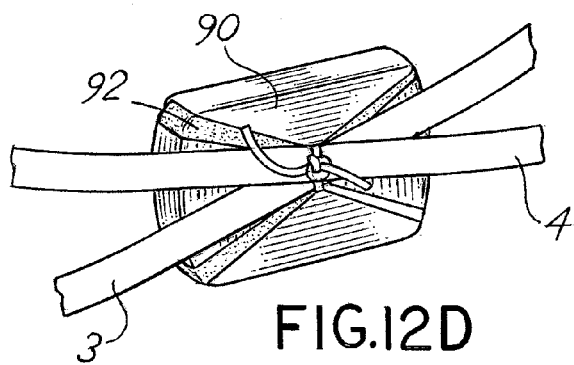

The pad support and adjustable attachment means are shown in more detail in FIGS. 12A to 12D. The pad support is shown in FIG. 12A. As can be seen in FIG. 12B, the adjustable attachment element comprises a pad wrapping material 90 formed by a sheet having strips (ties) 91 provided at its corner regions. The pad wrapping material 90 may comprise a polyester or rubber material. The pad support 92 is wrapped inside of the pad wrapping material and the pad wrapping material is securely fastened around the pad support using two of the strips, as shown in FIG. 12C. The remaining two strips are then used to tie the pad support/pad wrapping material assembly around the two crossed tensioning straps, as can be seen in FIG. 12D. In this manner, the pad support 92 can be securely attached to the tensioning straps and can also be free to move laterally along the straps. One or more additional pads may be attached to the outer surface of the pad wrapping material 90.

In a modification of each of the above described first to fourth embodiments, one or more additional pads may be attached to the tensioning straps at a position or positions different from that of the above described adjustable attachment elements. Such pads may be attached to one of the tensioning straps using an adhesive material, for example. Thus, the lumbar support devices may be configured to best suit a particular patient's needs.

FIG. 13 shows a rear view of a user wearing a selective stabilization support device according to a fifth embodiment of the invention. The selective stabilization support device of this embodiment is designed to provide selective support to a mid-back region of a user. Furthermore, the device may be adapted so as to provide selective support to a lower neck region also.

As can be seen in FIG. 13, the selective support device comprises a pad holder 51 positioned at a mid-back region of the user. A pad 52 is provided inside of the pad holder, the pad being removable from the pad holder. Attachment means 53 may be provided on the holder 51 to enable the attachment and removal of straps to and from the holder, the straps being provided to maintain the pad and holder securely in position. The attachment means may comprise regions of adhesive material. Alternatively, the straps may be provided with clips for attachment to the pad holder. Two transverse stabilization straps 55, 56 are provided, each attachable at a first end region to the holder and each extending, in use, over a shoulder of the user and substantially vertically down the chest and torso of the user to terminate at a second end region at a leg portion of the user, as shown in FIG. 14. Two diagonal support straps 57, 58 are also provided, each attached at a first end region to the holder and each extending, in use, away from the holder around a side of the user to attach at a second end region to a respective one of the transverse stabilization straps. Furthermore, a lateral stabilization strap 54 is provided, the lateral stabilization strap being connectable to the attachment means of the holder and extending substantially horizontally around the back and chest of the user when in use.

In addition, in the embodiment of FIG. 13, a neck stabilization strap 59 is also provided, the neck stabilization strap running diagonally across the user's back and chest and being secured to the holder 51 or other straps by means of regions of adhesive material. A lower neck selective stabilization support pad 60 is mounted on the neck stabilization strap at a lower neck region of the user. The lower neck selective stabilization support pad 60 may be attached to the neck stabilization strap by means of an adhesive material, and is preferably detachable from the strap. Alternatively, the lower neck selective stabilization support pad 60 may be attached to one of the transverse straps 55, 56, as opposed to being provided on its own strap 59. The lower neck selective stabilization support pad enables localized support to be applied to a chosen area of the user's lower neck.

FIG. 14 shows a front view of the user wearing the selective stabilization support device according to the fifth embodiment of the invention. As can be seen in FIG. 14, an anterior stabilization strap 61 may be provided between the transverse stabilization straps. The anterior stabilization strap 61 is positioned across the user's torso below the lateral stabilization strap, and is attached to one of the transverse stabilization straps at a first end and to the other transverse stabilization strap at a second end. It can also be seen in FIG. 14 that clips 62 may be provided at the said second end region of each of the transverse stabilization support straps 55, 56, the clips being for attachment to the socks of the user. In addition, leg loop straps 63 may be provided around the legs of the user, each leg loop strap being attached to one of the said transverse stabilization straps 55, 56, for example by means of a region of adhesive material provided on the leg loop strap and/or on the transverse stabilization strap. Preferably two leg loop straps are provided on each leg of the user, one of the leg loop straps encircling the user's thigh, the other leg loop strap encircling the user's calf. Furthermore, each of the transverse stabilization straps 55, 56 may comprise a central loop strap 64 located at a kneecap region of the user. Each central loop strap forms a loop connected at top and bottom portions to the vertically extending section of its transverse stabilization strap. In addition, a leg loop knee strap 65 may be attached to each of the central loop straps at left and right portions of the central loop strap, the leg loop knee strap extending generally horizontally around the back of the user's knee. By providing straps in this manner around each of the knees of the user, the user's freedom of movement about each knee joint is ensured.

Figure 15:
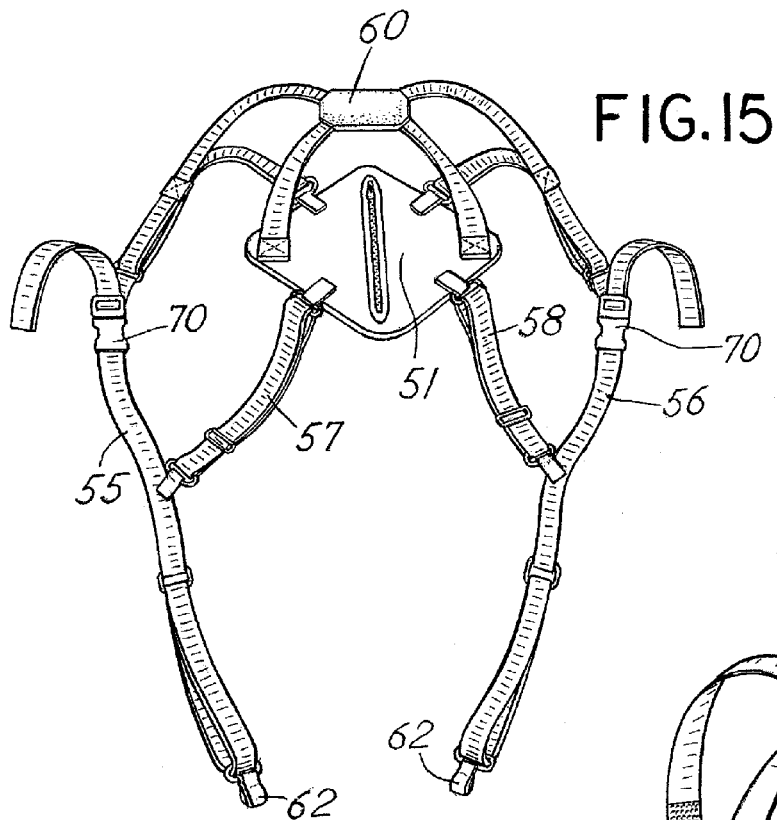
FIG. 15 shows a rear view of a stabilization support device according to a modification of the fifth embodiment of the invention.

FIG. 15 shows a rear view of a selective stabilization support device according to a modification of this embodiment. In FIG. 15, the transverse stabilization support straps 55, 56 and the diagonal support straps 57, 58 are attached to the holder 51 by means of metal clips. The lower neck selective stabilization pad 60 is provided as a central lower neck pad, and is attached to the holder by means of straps adhered to adhesive regions of the holder. It can also be seen in this figure that adjustment means in the form of buckles 70 are provided on the transverse stabilization straps, to enable the length and tension of those straps to be adjusted. By adjusting the tension of the transverse stabilization straps, the device can be comfortably fitted and secured effectively. Moreover, it can be ensured that the desired force is applied to the mid-back region of the user.

Figure 16C:
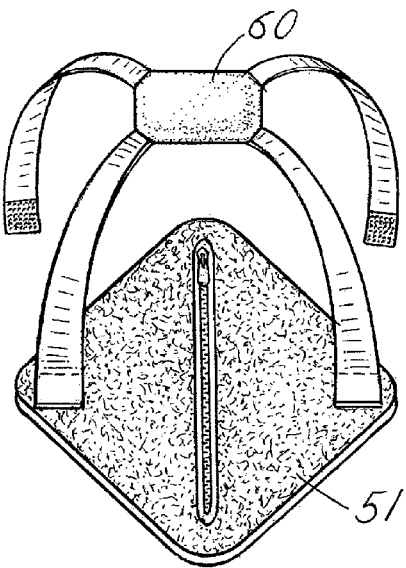
FIGS. 16A to 16C show the configuration of a holder and a support pad of the stabilization support device of FIG. 15.
Figure 16B:
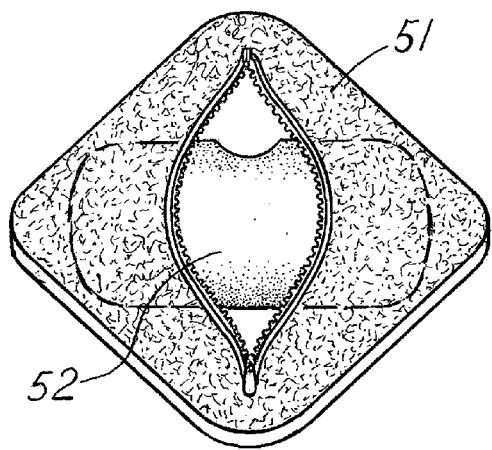
Figure 16A:
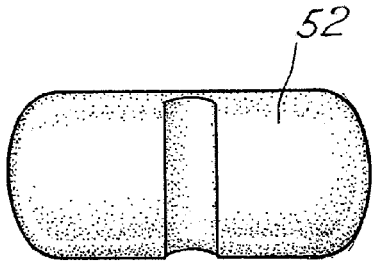

As already mentioned above, the pad support 52 is enclosed within the pad holder 51. A more detailed view of the pad support, pad holder and central lower neck pad 60 is shown in FIGS. 16A to 16C. If the pad support is to be positioned centrally on the user's spine, then the pad support may be formed with an indention contoured to the shape of the spine so as to relieve the pressure on the spine, as shown in FIG. 16A. The pad support 52 may be placed inside of the pad holder 51 by means of a zip provided on the pad holder, as can be seen from FIG. 16B. FIG. 16C shows the central lower neck support attached to the holder 52 using attachment means comprising adhesive regions formed on the holder 52. Furthermore, similar adhesive attachment means may be provided on the upper straps of the central lower neck support in order that these straps may be attached to the transverse stabilization straps of the device.

Furthermore, additional pads may be attached to the pad holder to generate the required pressure on a localized area of the user's mid-back region. Accordingly, as in the first to fourth embodiments, different pad sizes, shapes and densities may be chosen by a therapist to best suit the user's individual needs for selective stabilization. Thus, pads of various shapes such as those shown in FIGS. 5A to 5G may be used.

The lumbar support and selective stabilization devices according to the various embodiments of the invention enable selective stabilization of a patient's back to be achieved for long periods of time. In particular, the lumbar support devices are designed specifically to centralize mechanical lumbar radiating pain in a manner that complements the McKenzie approach to mechanical back pain.

Furthermore, lumbar support devices according to embodiments of the invention are versatile, enabling the required selective stabilization to be performed at a required lateral and medial position. In particular, the movable adjustable attachment element enables the pads to be positioned at the precise location required. Furthermore, the different pad sizes, shapes and densities, together with the tensioning straps, allow for adjustment of the applied pressure to suit the particular needs of the patient.

In addition, the semi-rigid abdominal member prevents excessive trunk bending by the patient, and thus helps to prevent the occurrence of further damage. This member, together with the pads, also helps to teach correct posture to the patient. Furthermore, the device allows some spinal movement. If the spine is immobilized to too great an extent, this can be detrimental to the segments above and below the disk lesion, particularly if the spine is immobilized for a large period of time. For example, if the spine does not move adequately, over a prolonged period, to allow synovial fluid to bathe cartilage between facet joints, this can predispose an individual to accelerated osteoarthritis in these regions. Here, advantageously, the lumbar support device provides selective stabilization where it is required, but allows the spine to move in the regions where the selective stabilization is not required.

Thus, according to a further embodiment of the present invention, a method of treating mechanical lower back pain is provided. The method entails the use of the McKenzie or a similar technique to determine the nature of the patient's lower back pain, and the fitting of a lumbar support device, as described to help to treat the pain in combination with the mobilization and other exercises of the McKenzie or other technique.

FIGS. 17 through 25 illustrate a further embodiment of the invention which comprises a selective stabilization lumbar support including a flexible torso belt that fits around the midsection of an individual in combination with a strap assembly and a pressure appliance arm that in combination enable the placement of a customized pressure pad against a selected spot or position on the torso of an individual, most typically on the back of an individual. Referring to the figures, the lumbar support includes a torso belt 100 which is adequately flexible to fit around the midsection of medial portion of the torso of an individual and which further includes means for engaging a first end 102 to a second end section 104 of the torso belt 100. In the embodiment shown, the interior face or surface 106 of the torso belt 100 includes hook and loop material 110 (e.g. Velcro fastener) which cooperates with a hook and loop material 114 on the outside surface 112 of the torso belt 100. In this manner, the torso belt 100 may be placed around the midsection of an individual and adequately tightened to maintain belt 100 in position in combination with the other elements associated with the lumbar support embodiment.

The torso belt 100 thus, has a longitudinal dimension which is adequate to fit around the torso of an individual and a height dimension which is adequate to engage with and support a series of fasteners and elements described hereinafter including an associated strap assembly. Typically the dimensions of the torso belt 100 in the vertical direction as contrasted with the longitudinal direction is in the range of 6 to 18 inches although other dimensions may be utilized depending upon the size of the individual which is to be accommodated by the lumbar support apparatus or device. Typically belt 100 is generally rectangular; however, belt 100 may be otherwise configured in order to comfortably fit around a torso, for example, belt 100 may include curved upper and lower longitudinally extending edges or margins.

The outside face 112 of the lumbar support torso belt 100 may further includes some hook and loop fastener material 114 (eg. Velcro brand) along at least medial portion of the outside surface 112. Thus, the hook and loop material 114 on the outside surface 112 will extend over a significant range or portion of the outside surface 112 although such inclusion in the device is or may be optional.

Incorporated in the second end section 104 on the outside surface 112 adjacent the hook and loop material 110 is a series of fastener elements. The fastener elements or fastener element assembly 116 comprises a series of rings or D loops arranged in pairs and fastened by straps to the outside face or surface 112 of the belt 100. In the embodiment depicted, six arrays of dual D rings or D loops, which are typically metal rings or metal loops, are arrayed in a vertical pattern on the outside face 112 of the torso belt 100. Each of the separate combinations of loops and D rings is substantially identical in the embodiment depicted. Thus, for example, a first D ring 118 and a second D ring 120 are engaged by a strap 122 sewn to the outside surface 112 of the torso belt 100. In the embodiment depicted, a series of six combinations of dual D rings and associated loops are provided and arrayed as a first group of vertical array of D rings and loops 124 and a second parallel, adjacent array of such D rings and loops 126. The number of arrays and their positioning may be varied depending upon the particular needs and desires with respect to the lumbar support device. In the embodiment depicted, the first array 124 is comprised of three sets of D rings and loops as is the second array 126. The arrays 124, 126 are aligned vertically with respect to each other. However, they may be positioned at other desired places and orientations on the outside surface 112 of the torso belt 100 in order to facilitate the objectives of the combination. Thus, the number and placement of the loops and D rings is subject to design modifications that vary from the specific embodiment depicted for example in FIG. 20.

The D rings 118, 120 are designed to be cooperative with one or more elongate straps. In the embodiment depicted, three, elongate straps 128, 130 and 132 are provided. Each of the straps 128, 130 and 132 in the embodiment depicted include opposite outer ends such as end 134 and end 136 of strap 130. The outer ends 134, 136 of the strap 130 and the other straps 130 and 132 include hook and loop fastener material 140 with adjacent compatible hook and loop material 142 to enable the strap 130 to be fitted through a D ring such as D ring 119 and folded to be retained thereby as depicted, for example, in FIG. 21. Each end 134, 136 of each of the straps 128, 130 and 132 has a similar construction thereby enabling each of the straps 128, 130 and 132 to be engaged with an appropriate D rings to fasten each of the straps 128, 130 and 132 about the torso of an individual as depicted for example in FIG. 17, 18 or 19. It is to be noted that the ends of the straps such as 134 to 136 may be color coded to facilitate the utilization of the lumbar support device and the engagement of and placement of the straps such as strap 128 about the torso of an individual and to further facilitate the connection thereof to the appropriate D rings.

Figure 21:
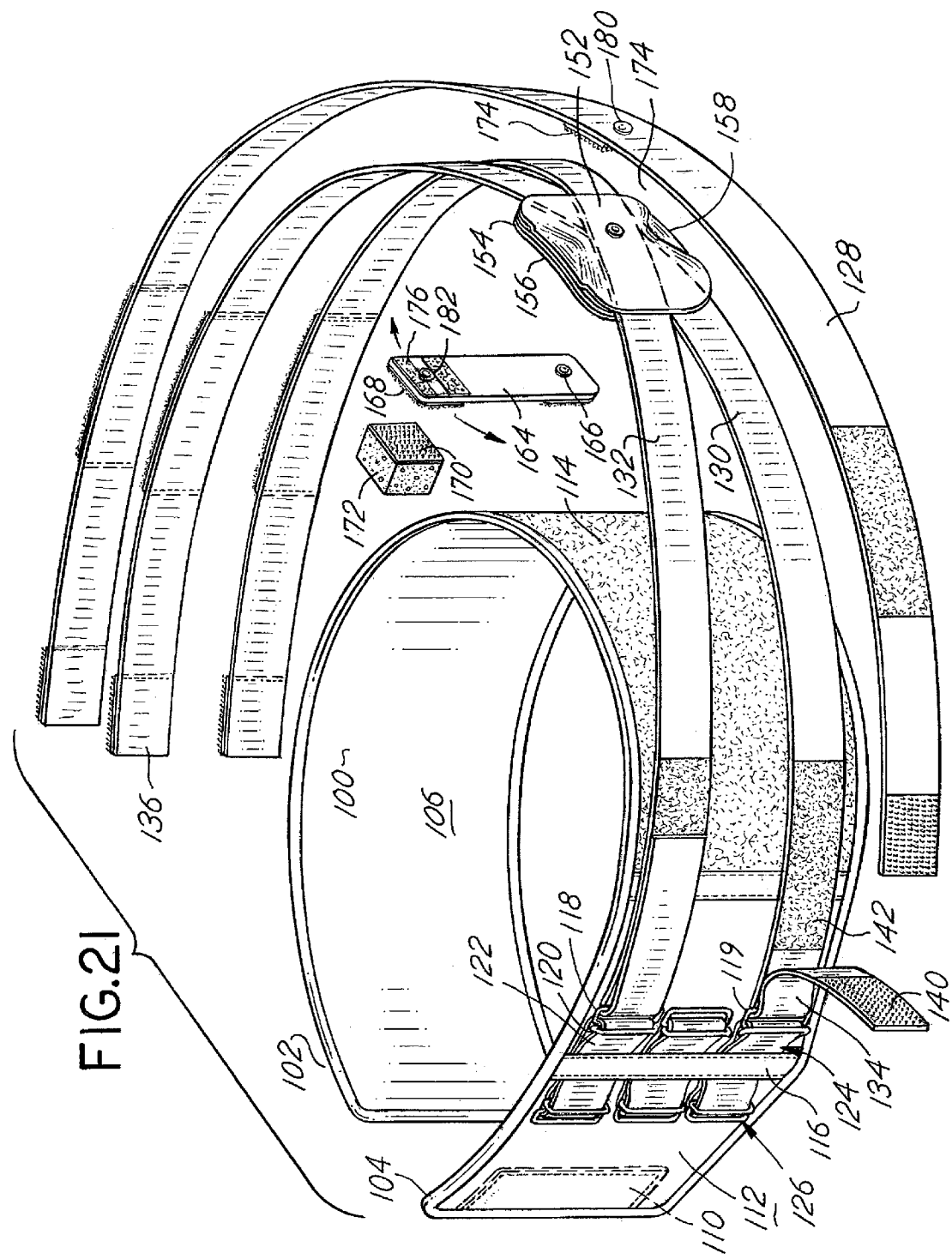
FIG. 21 is an exploded isometric view of the embodiment of FIG. 19.

A further element included in the combination is a guide member 150. The guide member 150 comprises two layers or spaced sides of material, for example, as illustrated in FIGS. 21 and 23; namely, a first outer layer 152 and a second inner layer 154 which together define a through pocket therebetween inasmuch as the layers or sides 152, 154 are joined along a top edge or margin 156 and a bottom edge or margin 158 provide to or define a through pocket between the layers 152 and 154. In this manner, straps such as straps 130 and 132 may be extended or positioned through the pocket or passage defined by the layers 152 and 154. The straps 130 and 132 are thus constrained by the guide member 150 at least to some extent and the opposite ends of the straps 130 and 132 may then be fastened to D rings such as D rings 118 and 119 to thereby position generally in a precise manner the guide member 150. The inner layer 154 may also include hook and loop fastener material 155 for cooperative engagement and retention of guide member 150 on the torso belt 100 by engagement with fastener material 114.

The guide member 150 further includes a fastener mechanism 160 on the inside surface of the layer 154 and also includes a fastener member 162 on the outer surface of the outer layer 152. The fasteners 160 and 162 are generally placed in the middle of the guide member 150. However, other alternative positions and additional fasteners may be incorporated in the guide member 150. For example, a second guide member 162A could be incorporated on the outside surface of the guide member 150. In similar fashion additional fasteners could be incorporated and included on the inside layer 154 of the guide member 150. Again, the position of the fasteners 160, 162 and 162A is subject to the desires of the design embodiment to be provided of the lumbar support device.

By attaching straps 130 and 132, by way of example, through the guide member 150 and ultimately attaching the straps 130, 132 to the torso belt 100 through engagement with appropriate D rings 118, 120, the guide member 150 can be desireably positioned on the backside or other portion of the torso belt 100. Most typically the guide member 150 is, however, positioned somewhere on the backside of an individual wearing the torso belt.

Figure 25:
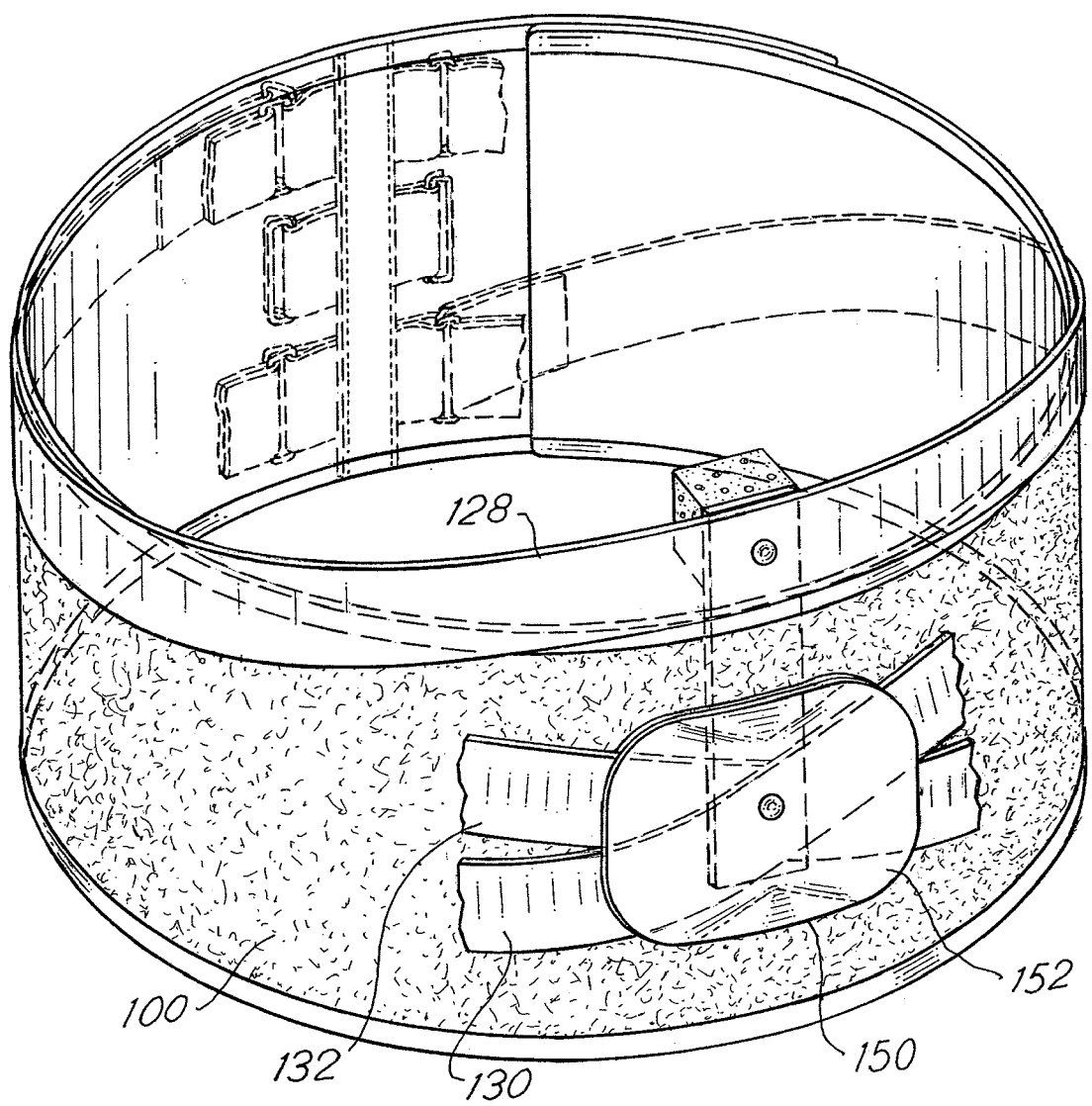
FIG. 25 is a partial isometric view of the lumbar support embodiment of FIG. 21 in an assembled condition.

As a further feature of the invention, a pressure appliance arm 164 is provided. The arm 164 in the embodiment depicted comprises a planar member having an internal end fastener 166. The fastener 166 is designed to be engaged with and connect to the fastener 160 such as illustrated in FIG. 24. In this manner, the arm 164 is engaged and its inner end or lower end is positioned by virtue of the positioning of the guide member 150. Thus, as illustrated in FIG. 25, the arm 164 may be positioned in any of a number of positions with respect to the torso belt 100 by the arranged combination with the straps 130 and 132 and positioning guide member 150 on torso belt 100.

The arm 164 extends radially or outwardly from the connected fasteners 160/166 and may be rotated as desired and as depicted by the arrows in FIG. 21. In a typical embodiment, the outer end of the arm 164 includes a fastener element 168 which is cooperative with a fastener element 170 attached to a pressure appliance 172 such as a shaped foam rubber or foam block. Various materials may be used for the pressure appliance or pad 172. Various shapes of pad 172 may also be incorporated depending upon the desires and needs with respect to the use of the lumbar support device. The position of the pressure member 172 is thus highly adjustable and may be positioned on the back side of a person, for example, as depicted in FIG. 19 at a desired or therapeutically beneficial pressure point and maintained in that position. To help maintain the pressure pad 172 in position, a third strap such as strap 128 may be engaged with or placed against the arm 164 again as illustrated in FIG. 19. The inside surface of the strap 130 may include a hook and loop fastener material 174 cooperative with hook and loop fastener material 176 on the backside or outside face of the arm 164 such as illustrated in FIG. 19 or 21. In this manner, the strap 128 may be appropriately positioned and engaged with D rings such as D rings 118 and 120 of the torso belt 100 to thereby maintain the pressure pad 172 in a desired position against the backside of an individual in a therapeutically beneficial manner. Of course, other fastener means other than the hook and loop fastener materials may be substituted. Alternating for example, a fastener 180 on the inside face of strap 128 may snap into fastener 182 on arm 164 to hold the arm 164 in a fixed position.

Other variations may be incorporated with respect to the embodiment depicted. For example, the length and shape and of the arm 164 may be varied. The arm 164 may, for example, be bifurcated at its outer end or broadened. Additionally, the dimensions and length of the straps such as straps 128, 130 and 132 may be varied. The configuration shape and placement of the pressure pad or pressure element 172 may be varied and the position and number of pads 172 along the length of the arm 164 may be varied. The pressure pad 172 may extend outwardly from the sides of the arm 164. Many other variances may be imported into the design of the various elements set forth. For example, the number of straps involved with respect to the invention as depicted in the embodiment as shown comprises three straps. However, the utilization of three straps should not be considered a limitation of the invention. Two, three, four or more straps can be useful in the combination utilizing the appliance arm and the pressure pad for example. Thus, a single strap may be fitted through the guide member 150 and a further strap may be utilized to maintain the position of a pressure pad 172 on the appropriate portion or torso of an individual.

Further, besides being a passive tool to help reduce disc lesions (and to selectively stabilize), the brace may be used as an active exercise enhancer. When wearing the brace or support, it has the ability to assist with Mckenzie extension exercises creating more selective extension of the spine by helping to obtain end range mobility. When used appropriately, for individuals with restrictive soft tissue and/or scar tissue tightness (in the torso), it can help to remodel this tissue at the desired level promoting improved mobility and self management. For injury recovery, often scar tissue (especially after acute inflammation) needs to be stretched, remodeled, and made more pliable.

In review, for some populations with radiating leg pain, the brace can help centralize pain and improve motor function allowing them to walk better. For some individuals with restrictive trunk soft tissue tightness, it can help enhance mobility exercises improving pliability and function (i.e. allowing someone to extend their back more and better reach in to kitchen cabinets). For some with disc derangements, it can help (in conjunction with McKenzie exercises) to reduce them and selectively stabilize them (through selective mobilization) and allowing it to heal (through selective stabilization). In some populations with poor posture, it can act as a retraining tool and proprioception enhancer and address muscle imbalances in the trunk and shoulder regions. For some older individuals who are weak, it can help them maintain better (more neutral) posture until they have more stamina and trunk stability. By improving posture and muscle imbalances it can reduce neck pain in some individuals (by improving the neck's base of support).

While, there has been set forth embodiments of the invention, it is to be understood that the invention is to be limited only by the following claims and the equivalents thereof.

What is claimed is:

1. A selective stabilization lumbar support comprising:
   a flexible material torso belt having a longitudinal dimension, a lateral width generally transverse to the longitudinal dimension, a front side, a back side for positioning against the torso of an individual, a first end section, an opposite second end section, a fastener assembly for attaching the first end section to the second end section to maintain the belt fitted over the torso of an individual, and an assembly of strap attachment connectors on the front side;
   a strap assembly, said strap assembly including first, second and third elongate straps, each of said straps having first and second opposite end sections and a medial section, said end sections each including fastener devices for connection to said strap attachment connectors of said belt,
   a strap guide member, said guide member including a strap passage for receipt of said first and second straps therethrough;
   said strap guide member including an inside face with an appliance fastener;
   a pressure appliance arm including a first coupler mechanism for attachment of the pressure appliance arm to the appliance fastener of the strap guide;
   said pressure appliance arm fastener further including a pressure appliance to position upon a torso; and
   said third strap including a medial section fastener for engaging and retaining the pressure arm in a generally fixed position.

2. The support of claim 1 wherein said pressure appliance arm is rotatably adjustable about said first coupler mechanism.

3. The support of claim 1 wherein said pressure appliance is removably fastened to the pressure appliance arm.

4. The support of claim 1 wherein said pressure appliance is adjustably positioned on the pressure appliance arm.

5. The support of claim 1 wherein the strap connectors comprise an array of at least one row of ring elements mounted to the torso belt generally transverse to the longitudinal dimension.

6. The support of claim 1 wherein end sections of the straps are color coded.

7. The support of claim 5 wherein the strap connectors comprise an array of two adjacent rows of ring elements.

8. The support of claim 1 wherein the pressure appliance arm comprises an elongate, planar plate rotatably attached to the strap guide member.

9. The support of claim 1 wherein said attachment connectors are arrayed on the first end section.

10. The support of claim 1 further including additional medial strap fastener elements on the outside face of the torso belt and said third strap including cooperative medial fastener elements for engagement with said additional medial fastener elements of said torso belt.

11. A selective stabilization lumbar support comprising:
- a flexible material torso belt having a longitudinal dimension, a lateral width generally transverse to the longitudinal dimension, a front side, a back side for positioning against the torso of an individual, a first end section, an opposite second end section, a fastener assembly for attaching the first end section to the second end section to maintain the belt fitted over the torso of an individual, and an assembly of strap attachment connectors on the front side;
- a strap assembly, said strap assembly including at least first and second elongate straps, each of said straps having first and second opposite end sections and a medial section, said end sections each including fastener devices for connection to said strap attachment connectors of said belt,
- a strap guide member, said guide member including a strap passage for receipt of first strap therethrough;
- said strap guide member including an inside face with an appliance fastener;
- a pressure appliance arm including a first coupler mechanism for attachment of the pressure appliance arm to the appliance fastener of the strap guide;
- said pressure appliance arm fastener further including a pressure appliance to position upon a torso; and
- said second strap including a medial section fastener for engaging and retaining the pressure arm in a generally fixed position.

12. The support of claim 11 wherein said pressure appliance arm is rotatably adjustable about said first coupler mechanism.

13. The support of claim 11 wherein said pressure appliance is removably fastened to the pressure appliance arm.

14. The support of claim 11 wherein said pressure appliance is adjustably positioned on the pressure appliance arm.

15. The support of claim 11 wherein the strap connectors comprise an array of at least one row of ring elements mounted to the torso belt generally transverse to the longitudinal dimension.

16. The support of claim 11 wherein end sections of the straps are color coded.

17. The support of claim 15 wherein the strap connectors comprise an array of two adjacent rows of ring elements.

18. The support of claim 11 wherein the pressure appliance arm comprises an elongate, planar plate rotatably attached to the strap guide member.

19. The support of claim 11 wherein said attachment connectors are arrayed on the first end section.

20. The support of claim 11 further including additional medial strap fastener elements on the outside face of the torso belt and said third strap including cooperative medial fastener elements for engagement with said additional medial fastener elements of said torso belt.

* * * * *